United States Patent [19]
Briggs et al.

[11] Patent Number: 5,962,764
[45] Date of Patent: Oct. 5, 1999

[54] FUNCTIONAL CHARACTERIZATION OF GENES

[75] Inventors: Steven P. Briggs; Robert B. Meeley, both of Des Moines, Iowa

[73] Assignee: Pioneer Hi-Bred International, Inc., Des Moines, Iowa

[21] Appl. No.: 08/835,638

[22] Filed: Apr. 10, 1997

Related U.S. Application Data

[63] Continuation of application No. 08/262,056, Jun. 17, 1994, abandoned.

[51] Int. Cl.$^6$ .............................. A01H 4/00; C12N 15/09
[52] U.S. Cl. ......................... 800/270; 800/267; 800/275; 800/298; 800/320.1; 536/24.1; 536/23.6; 536/24.33
[58] Field of Search ................................. 800/320.1, 270, 800/266, 298, 267, 275; 536/24.1, 23.6, 24.33

[56] References Cited

U.S. PATENT DOCUMENTS

| | | | |
|---|---|---|---|
| 4,732,856 | 3/1988 | Federoff | 435/172.3 |
| 5,004,864 | 4/1991 | Robertson et al. | 800/235 |
| 5,432,068 | 7/1995 | Albertson et al. | 435/172.3 |

OTHER PUBLICATIONS

Coe et al. (1977) Corn and Corn Improvement, Ed. G.F. Sprague et al.. ASA publication No. 18. pp. 135–137.

Marks et al. "Trichome development in Arabidopsis thaliana." The Plant Cell vol. 1, pp. 1043–1050, Nov. 1988.

Feldman et al. "A dwarf Mutant of Arabidopsis generated by T–DNA Insertion Mutagenesis" Science. vol. 243 pp. 1351–1354, Mar. 3, 1989

Walbot, V. Annu. Rev. Plant Physiol. vol. 43, pp. 49–82, 1992.

Ballinger et al. "Targeted Gene Mutations in Drosophila," *Proc. Natl. Acad. Sci. USA*, 86: 9402–9406 (Dec. 1989).

Kaiser et al. "Site–Selected" Transposon Mutagenesis of Drosophila, *Proc. Natl. Acad. Sci. USA*, 87: 1686–1690 (Mar. 1990).

Zwaal et al. "Target–Selected Gene Inactivation in *Caenorhabditis elegans* by Using a Frozen Transposon Insertion Mutant bank," *Proc. Natl. Acad. Sci. USA*, 90: 7431–7435 (Aug. 1993).

Rushforth et al. "Site–Seleeteed Insertion of the Transposon Tc1 Into A *Caenorhabditis elegans* Myosin Light Chain Gene," *Molecular and Cellular Biology*, 13(2): 902–910 (Feb. 1993).

*Primary Examiner*—Gary Benzion
*Attorney, Agent, or Firm*—Pioneer Hi-Bred International, Inc.

[57] ABSTRACT

Insertions into a gene of known sequence can be generated by crossing two parent plants, one of which contains a transposable element, to produce $F_1$ progeny plants in which the insertion is detected by means of a PCR. $F_1$ progeny plants containing such an insertion are self-fertilized to produce $F_2$ progeny which are homozygous for the insertion. The function of a gene disabled by the insertion can be ascertained from a comparison of the phenotype of the $F_2$ progeny with a parental phenotype. Large numbers of $F_1$ progeny can be tested simultaneously for the presence of insertions. A collection of $F_2$ seed can be stored and used for phenotype comparison when an insertion is detected.

11 Claims, No Drawings

FUNCTIONAL CHARACTERIZATION OF GENES

This application is a continuation of application Ser. No. 08/262,056, filed Jun. 17, 1994 abandoned.

BACKGROUND OF THE INVENTION

Modern advances in recombinant DNA technology have made possible the cloning and sequence determination of many genes, the functions of which remain to be determined. Methods have been developed for ascertaining the functions of these genes and may be divided into three main types.

The first method involves the sequestration of the messenger RNA corresponding to the gene sequence of interest by an antisense oligonucleotide or nucleotide analogue complementary to the sequence of the RNA. This prevents initiation of translation of the messenger RNA by the ribosome, and production of the protein product of the gene is thereby suppressed. The function of the gene is therefore imputed from observation of a mutant phenotype induced by this suppression. Introduction of the antisense oligonucleotide may be achieved either by transfection of the target cell with a suitable gene construct which directs production of an antisense transcript within the cell, or by direct introduction of exogenous oligonucleotides or oligonucleotide analogues into the cell.

Although the antisense method has been successful in model systems such as cultures of dissociated cells, its implementation in a whole organism is problematic. For example, simultaneous delivery of exogenous oligonucleotides to all tissues of interest in a whole organism is extremely difficult. Exogenous oligonucleotides are also metabolized by cells, and any phenotype produce by this method is therefore only temporary. To preserve a desired mutant phenotype for prolonged study the mutation must be made heritable by creation of a transgenic organism. This requires that a gene construct coding for the antisense RNA be stably creation of a transgenic organism. This requires that a gene construct coding for the antisense RNA be stably transfected into the germ cells of the organism under study, followed by rounds of inbreeding of transgenic progeny to make organisms homozygous for the mutation. Creation of transgenic organisms is therefore typically a laborious and expensive process.

A second approach to determine the function of a gene of known sequence is by the "co-suppression" technique, which also requires the creation of a transgenic organism. In this approach the transfected gene construct codes for the gene of interest in the sense orientation, and a small proportion of the transformants exhibit loss of function of the gene of interest via an unknown trans mechanism. As with the antisense approach this method suffers from the disadvantage of requiring the creation of a transgenic organism.

A third approach is to disrupt the gene of interest by transformation of target cells with a vector designed to stably integrate into the host chromosome within the coding sequence of the gene of interest, via the process of homologous recombination. Since homologous recombination is a rare event, this approach typically utilizes a targeting vector designed to introduce a gene for antibiotic resistance normally lacking in the target cells, allowing selection of the small number of desired transformants. Integration of the antibiotic resistance gene within the coding sequence of the gene of interest in this fashion also serves to disrupt normal transcription of the gene, producing an aberrant, non-functional protein product. This approach also requires germ-line transmission of the disrupted gene for subsequent generation of organisms homozygous for the mutation, and therefore also suffers from the disadvantages discussed supra.

A more recent method to cause gene disruption has been the use of naturally occurring transposable elements to introduce gene insertions, together with the use of a PCR to detect an insertion event within a particular gene of interest. Ballinger et al., *Proc. Nat'l Acad. Sci.* 86: 9402-06 (1989); Kaiser et al., loc. cit. 87: 1686-90 (1990); Zwaal et al., loc. cit. 90: 7431-35 (1993). In this method two oligonucleotide primers were employed in the PCR, with one primer complementary to a sequence within a particular gene of interest, and the other primer complementary to a portion of the tandem inverted repeat sequence of the transposable element.

Both Ballinger et al. and Kaiser et al. crossed parental strains of the fruit fly *Drosophila melanogaster,* one strain of which carried a transposable element, to produce a pool of heterozygous $F_1$ progeny bearing genome insertions caused by the transposable element. Ballinger et al. then screened the genomic DNA of the $F_1$ progeny for the presence of insertions in two genes of unknown function, as described above. Flies in which the desired gene insertions were observed were then used to produce $F_2$ progeny homozygous for the insertion, and their phenotype examined for effects attributable to the absence of function of the gene of interest. But no phenotypic changes from the wild type were observed for any $F_2$ flies which were homozygous for insertions into either gene of interest.

Kaiser et al. carried out the screening for gene insertions using the DNA of the segregating $F_2$ generation of flies, rather than at the $F_1$ generation. Insertions were observed into a gene which was previously known to produce a specific phenotype when disrupted by insertion, and the expected phenotype was observed. In this fashion Kaiser et al. demonstrated that disruption of a known gene by insertion of a transposable element could be correlated with observation of a previously known phenotype.

An additional problem associated with DNA analysis of the $F_2$ generation instead of the $F_1$ generation is the possibility of observing additional insertion events into the gene of interest caused by the activity of the transposable element during generation of the $F_2$ generation. These mutant alleles will be detected by DNA analysis of the $F_2$ generation, but as they will not genetically segregate until the next gametic cycle they will not contribute to the homozygous genotype of the $F_2$ generation. Accordingly, DNA sampling at the $F_2$ generation will lead to the identification by PCR of insertion events in the gene of interest which will not be reflected in the phenotype of the $F_2$ generation, generating false positive results which require further experimentation to detect.

Zwaal et al., working in the worm *Caenorhabditis elegans* (*C. elegans*), also carried out PCR analysis for gene insertion events caused by a transposable element in the DNA of the $F_2$ and subsequent generations. In addition the Tc1 transposable element was used which also generated deletion mutants in the $F_2$ and subsequent generations caused by the transposable element "jumping" from the initial site of insertion and excising some amount of DNA from the region of the gene flanking the insertion site. Despite the detection of 23 insertion events into 16 known genes and 7 deletion events in 6 known genes, no phenotypic difference from the wild type was observed in any of the $F_2$ worms or subsequent generations.

Zwaal et al. also described the production of libraries of $F_2$ progeny of *C. elegans* in a frozen state. These libraries could be used both to prepare DNA for PCR analysis as described above, and to recover viable worms for subsequent phenotypic analysis. Use of such libraries could in principle obviate the need to generate new collections of mutant progeny in order to analyze the function of each new gene of interest. The libraries disclosed, however, allow the preparation of only small quantities of DNA which may be sampled only a limited number of times, and which are insufficient for distribution to other laboratories. In order to detect insertions in more than a small number of genes, therefore, frequent generation of new libraries will still be required.

Although the aforementioned techniques are available for determining the function of a gene of known sequence, each conventional methodology has significant drawbacks, and the development of a rapid, inexpensive method would be highly desirable.

SUMMARY OF THE INVENTION

It is therefore an object of the present invention to provide a method for ascertaining the function of a gene for which the sequence is known.

It is also an object of the present invention to provide products, including genomic DNA collections and seed assemblages of particular constituency, that are particularly adapted to implementing such a method.

In accomplishing these objects, there has been provided, in accordance with one aspect of the present invention, a collection of genomic DNAs prepared from individual $F_1$ progeny plants obtained from crossing two parent plants, one of which contains a transposable element sequence, such that at least some of the $F_1$ progeny plants are heterozygous for insertion of the transposable element at a gene of known sequence, and where genomic DNA from each $F_1$ plant is present separately in the collection. In one preferred embodiment the collection is contained within the wells of a microtiter plate configured to allow automated sampling of the genomic DNA for PCR.

In accordance with another aspect of the present invention, there has been provided a collection of $F_2$ seed obtained by self-fertilization of the aforementioned $F_1$ progeny plants.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The present invention provides a novel method for determining the function of a gene of known sequence, and also provides products that facilitate the practice of the invention.

The invention is based on generating insertions into a gene of known sequence by crossing two parent plants, one of which contains a transposable element, to produce $F_1$ progeny plants in which the insertion is detected by means of a PCR. $F_1$ progeny plants containing such an insertion are self-fertilized to produce $F_2$ progeny at least some of which are homozygous for the insertion. The function of a gene disabled by the insertion can be ascertained from a comparison of the phenotype of the $F_2$ progeny with a parental phenotype. Large numbers of $F_1$ progeny may be tested simultaneously for the presence of insertions. The $F_2$ seed can also be stored and used for phenotype comparison when an insertion is detected in the genome of the corresponding $F_1$ plant. The 1:1 correspondence of DNA from an individual plant and the progeny from that individual plant is unique to this method.

In accordance with the present invention, a collection of genomic DNAs are prepared from numbers of $F_1$ plants produced by the crossing of two parent plants, one of which parents contains a transposable element. Sufficient DNA is prepared from each $F_1$ plant that the DNA samples can be used repeatedly to analyze for the presence of insertions into a large number of genes of interest, without the need to repeatedly generate new generations of $F_1$ or progeny plants. The invention relies on the use of a highly active transposable element which causes many insertion events per gametic cycle, thereby reducing the number of $F_1$ plants which must be produced in order to ensure an insertion occurs into any given gene of interest. In particular the invention contemplates the use of the highly active Mutator (Mu) family of transposable elements as a means of minimizing the number of $F_1$ plants required to ensure a desired insertion event. If a less active transposable element is used, correspondingly greater numbers of $F_1$ plants must be produced to produce the desired insertion.

Individual $F_1$ progeny plants are self-fertilized to produce a collection of $F_2$ seed, some of which $F_2$ plants will be homozygous for the gene insertion event of interest. The $F_2$ seed from each $F_1$ plant is kept separate, and these seed may be stored for extended periods of time for later germination and subsequent phenotypic analysis whenever a gene insertion event is detected in the corresponding $F_1$ parent plant as described above.

The present invention also provides a simple means of generating gene insertions which are heritable. Mutant phenotypes produced by the method of the invention may thus be preserved for further study by maintaining plants homozygous for the gene insertion. In addition, mutations that disrupt gametophyte development or function, or that are lethal in the homozygous condition, can be recovered and maintained in the heterozygous condition.

The present invention thus provides a rapid and inexpensive method of generating and detecting mutations in a gene of known sequence, which mutations cause loss of function of the gene. In particular, the present invention allows a function to be assigned to the gene by correlation with an observed mutant phenotype in organisms homozygous for the mutation.

A. Generation of $F_1$ Plants Heterozygous for Gene Insertion Events Caused by a Transposable Element An initial step in a method according to the present invention involves the crossing of two parent plants, one of which carries a transposable element, to produce a collection of $F_1$ progeny bearing gene insertions caused by the activity of the transposable element. A transposable element is a member of a class of diverse DNA segments that can insert into nonhomologous DNA in a manner independent of the general recombination function of the host. Most transposable elements carry terminal inverted repeat (TIR) sequences. These are DNA segments located at each terminus of the transposable element which share an identical sequence but are inverted with respect to each other. The present invention contemplates, but does not require, the use of a transposable element carrying a TIR.

Via the aforementioned cross, $F_1$ progeny are obtained by standard methods. In a preferred embodiment the plants are maize plants, and one parent plant carries the Mu family of transposable elements. Mu is the most mutagenic transposable element known. The other parent plant is preferably an inbred or hybrid strain, and in preferred embodiments is the B73 or A632 inbred strain or the Pioneer 3394 hybrid strain of maize. Insertion events caused by the transposable element occur at dispersed loci within the genome of the $F_1$ progeny plants produced by the crossing of the parent plants.

In a preferred embodiment, sufficient $F_1$ progeny are produced to ensure a high probability that many insertion events will occur in any given gene. For example in maize containing Mu, it is estimated that production of $10^5$ $F_1$ progeny will generate enough independent mutations to ensure a high probability that many insertion events will occur in any given gene.

B. Isolation of genomic DNA from the $F_1$ progeny

Genomic DNA can be isolated from plants using techniques that are well known in the art. See, for example, Taylor et al., "Isolation and characterization of Plant DNAs" in METHODS IN PLANT MOLECULAR BIOLOGY AND BIOTECHNOLOGY, Glick et al. (eds.), pages 38–41. For example, plant tissue can be ground after freezing in liquid nitrogen, extracted with a buffer containing the detergent CTAB, clarified by centrifugation to remove insoluble debris, and the resultant solution extracted with chloroform and isoamyl alcohol. DNA is precipitated by addition of buffer containing CTAB, collected by centrifugation, resuspended and purified on a cesium chloride density gradient. See Taylor et al., supra, at pages 38–41.

In a particularly preferred embodiment, six lyophilized leaf punches collected in 1.2 milliliter polypropylene tubes would be positioned in 96-well plates, with the positions recorded for identification of the source of the leaf punch. In a preferred method of DNA extraction, two stainless steel oil-free ball bearings are added to each tube containing the 6 leaf punches. The tubes are centrifuged briefly to position the ballbearings at the bottom of the tube, and the tubes are then sealed with mylar using a heat sealer. Using an apparatus capable of generating the necessary shaking movement, such as a modified jigsaw, the 96-well plates are shaken so that the integrity of the tissue is destroyed by the ball bearings. Six hundred microliters of extraction buffer are added to each tube, and the tubes are resealed and shaken again.

The plates are then heated for approximately 45 seconds in a commercially available microwave oven at high power, and then spun in a centrifuge at approximately 4,000 rpm for approximately 15 minutes. The supernatant is then added to fresh tubes containing isopropanol. The tubes are then mixed and centrifuged. The isopropanol is then decanted and as much isopropanol as possible is removed. The resulting pellets are dried, and 50 microliters of storage buffer may then be added, at which time the tubes are heated at 65° C. for 10 minutes to resuspend the pellet. For storage, the plate may be sealed with mylar using a heat sealer at approximately 380° C. and stored at −80° C.

In light of the fact that the present invention is directed to genetic analysis of large numbers of samples, at this point the original collection plates will have gone through a liquid handler and been reconfigured into either 4X or 9X plates. These are plates in which each well in the conventional 96-well microtiter plate format is replaced with a square array of 4 or 9 smaller wells, comprising respectively 384 or 864 wells in total. Using computer assisted tracking devices, any single well in the 9X plate can be referenced back to a well on the original 96-well plate from which a particular sample was obtained. In preferred embodiments of the invention, a 9X microtiter plate will typically be used, but the present invention also envisions use of 4X plates.

C. Analysis of the Genomic DNA from the F1 Progeny Plants by PCR

Genomic DNA isolated from the $F_1$ plants is used as target DNA for a PCR, where insertion of a transposable element within a gene of known sequence is detected by using one primer complementary to the gene of interest, and, in a preferred embodiment, one primer complementary to the terminal inverted repeat (TIR) sequence of the transposable element. Because the sequences of the terminal repeats of the transposable element are identical but inverted in orientation with respect to each other, a single PCR primer complementary to the repeat sequence will prime in both directions from the transposable element, ensuring that geometric amplification of DNA will occur, irrespective of the orientation of the transposable element, provided that the gene-specific primer anneals to the target DNA molecule within a sufficient distance of the annealing site of the TIR-specific primer. Primers complementary to non-palindromic insertion sequences of the transposable element may also be used. In this case, since the insertion may occur in either orientation, primers complementary to both strands of the transposable element are required to ensure detection of insertion events. Suitable oligonucleotide primer sequences may be designed by methods known in the art, based on the known sequences of the gene of interest and the TIR of the transposable element. See for example, Rychlik "Selection of Primers for Polymerase Chain Reaction" in METHODS IN MOLECULAR BIOLOGY, VOL. 15: PCR PROTOCOLS: CURRENT METHODS AND APPLICATIONS, B. A. White (ed), pages 31–40.

The PCR reaction can be run using protocols well known in the art. See for example, Delidow et al. "Polymerase Chain Reaction: Basic Protocols" in METHODS IN MOLECULAR BIOLOGY, VOL. 15: PCR PROTOCOLS: CURRENT METHODS AND APPLICATIONS, B. A. White (ed), pages 1–29. In a preferred embodiment of the present invention, an appropriate volume of PCR reaction solution is added to each well of a 9X microtiter plate. This may be done either manually or using a robotic liquid handler. Next, a defined amount of genomic DNA is added to the PCR reaction solution in each well, using either a pinner tool or manual addition techniques.

In preferred embodiments, unique steps are taken prior to addition of PCR reaction solution and DNA to the wells of the microtiter plates in order to prevent formation of gas bubbles during PCR. Due to the small volumes of the solutions used in the PCR the presence of bubbles can cause loss of sample during thermocycling. Hence, particular unique PCR buffers are used as described below, the microtiter plates are preheated prior to use, degassed water is used, and the plates are then centrifuged briefly prior to placing in an oven for the PCR reaction.

In a particular preferred embodiment, samples of DNA from 9X plates, each well of which contains genomic DNA from a single plant, are combined into pools containing DNAs from 48 individual plants. These pools are then transferred to a 9X plate, so that each well of the 9X plate contains DNAs from 48 plants, and in such a way that the contents of each pool may be referenced back to a collection of individual plant DNA samples. A 9X plate prepared in this manner is thus capable of holding DNAs from 41,472 plants. In a preferred embodiment, one third of the wells on the 9X plate are used for control samples, and each plate therefore can hold DNAs from up to 27,648 plants.

In an alternative preferred embodiment, 12 leaf punches are taken from each plant. Six punches from each plant are used to prepare individual DNA samples as described above. The remaining 6 leaf punches are combined in pools of punches from 48 different plants, and a mixed DNA solution is prepared from each pool as described above, except that the DNA is prepared in a 15 ml tube, using 6 ml of extraction buffer. The mixed DNA solutions are used to prepare 9X plates identical to those prepared by mixing the DNA samples as described previously.

Detection of PCR products may be carried out using methods well known in the art. See, for example, Allen et al., "The use of the Polymerase Chain Reaction and the detection of Amplified Products," in METHODS IN MOLECULAR BIOLOGY, VOL. 15: PCR PROTOCOLS: CURRENT METHODS AND APPLICATIONS, B. A. White (ed), pages 113–128. In a preferred embodiment PCR amplification products are detected by transferring samples of amplified DNA to a blotting membrane made of a suitable material such as nylon, followed by hybridization with a radioactively labeled probe derived from the gene of interest.

In a particularly preferred embodiment, following PCR the contents of the microtiter plates are transferred to a nylon membrane. Two membranes, which are preferably 8×12 cm, are presoaked in sterile, glass-distilled et al., "The use of the Polymerase Chain Reaction and the detection of Amplified Products," in METHODS IN MOLECULAR BIOLOGY, VOL. 15: PCR PROTOCOLS: CURRENT METHODS AND APPLICATIONS, B. A. White (ed), pages 113–128. In a preferred embodiment PCR amplification products are detected by transferring samples of amplified DNA to a blotting membrane made of a suitable material such as nylon, followed by hybridization with a radioactively labeled probe derived from the gene of interest.

In a particularly preferred embodiment, following PCR the contents of the microtiter plates are transferred to a nylon membrane. Two membranes, which are preferably 8×12 cm, are presoaked in sterile, glass-distilled water. The membranes are placed one at a time onto the top of the microtiter plate. Placement should be done with care so that no air bubbles remain trapped between the plate and the membrane, or between membranes. Blotting pads are then placed an top of the membrane layers, followed by a sheet of plexiglass, and the assembly is clamped and placed upside-down into a centrifuge. The blotting assemblies then are centrifuged to transfer the PCR-amplified DNA to the membranes, and the membranes carefully separated from one another. Prior to removing the last membrane the plate is placed back in the centrifuge right side up and centrifuged briefly again in order to remove the oil from the membrane. The DNA on the resulting membrane or "dot blot" is then cross-linked to the membrane, denatured and the membrane is prepared for hybridization.

The next step in the method of the present invention is hybridization with an appropriate labeled nucleic acid probe. Suitably labeled probes may be prepared and hybridized to the membranes containing the PCR products by methods known in the art. See, for example, CURRENT PROTOCOLS IN MOLECULAR BIOLOGY, Ausubel et al. (eds), pages 2.10.2–3 and 3.5.9–10. The membrane is then exposed to film (if a radioactively labeled oligonucleotide is used) in order to detect hybridization. Appropriate scanning software may be utilized in order to scan the resulting autoradiographs.

When hybridization of the labeled probe to one of the pools of DNA described above is observed, the PCR is repeated using as template the samples corresponding to the individual DNAs making up the pool. Transfer of the amplified products to a membrane and hybridization is then repeated as above to determine which individual DNA sample was responsible for the positive hybridization signal. Individual amplification products which give positive hybridization signals are then size-fractionated by agarose gel electrophoresis, with detection by staining with ethidium bromide. Observation of a discrete PCR product in the gel indicates that an insertion event has occurred within, or close to, the gene of interest. Confirmation that an insertion event occurred within a gene or a specific segment of a gene, rather than outside, can be obtained by repeating the PCR using additional gene-specific primers together with primers complementary to the transposable element. Since the structure of the gene of interest is known, analysis of the size of the products thus obtained and comparison with the sizes expected from the gene structure allows the site of the insertion to be estimated. Insertions that disrupt gene function can be selected by using primers that will identify insertions in the promoter region of the gene or in exons.

D. Production of $F_2$ progeny and assessment of phenotype

The $F_1$ progeny plants described above may be self-fertilized by standard methods known in the art to produce $F_2$ progeny. This step may be carried out prior to or subsequent to the DNA analysis described above. An $F_1$ plant which is heterozygous for gene insertions produced by a transposable element will, when self-fertilized, produce viable and non-viable $F_2$ progeny at least some of which will be homozygous for this gene insertion. When an insertion is detected in a gene of interest in a plant of the $F_1$ generation, the $F_2$ progeny of that plant are analyzed for a phenotype which differs from the expected wild-type phenotype, and which may be attributed to inactivation of the gene of interest by the insertion. A collection of $F_2$ seed can be prepared and stored for subsequent phenotypic analysis whenever mutations are identified in the corresponding collection of $F_1$ DNAs. The capability of generating large amounts of DNA from individual $F_1$ plants, taken together with the large numbers of $F_2$ seed produced from each $F_1$ plant means that analyses for insertions in a great many genes may be carried out without the need either to generate new $F_1$ progeny or to do breeding with the siblings or subsequent generations.

Phenotypic analysis of the $F_2$ plants may be carried by methods which are well known in the art. For example, visual examination and physical measurements will detect any gross changes in size or shape of any part of the plant. Similarly, microscopic examination will reveal changes in structural features which cannot be seen with the naked eye.

Phenotypic changes at the molecular level may be revealed by analysis of the expression of the mRNA or the protein product corresponding to the gene of interest. For example, patterns of expression of RNA in plant tissue may be examined by means of in situ hybridization, using a DNA or RNA probe specific for the gene of interest. Levels of expression of the mRNA corresponding to the gene of interest may be measured by means of Northern blots, using MRNA or total RNA preparations prepared from the whole plant or from particular organelles of the plant. Similarly mRNA corresponding to the gene of interest may be detected by the reverse transcription PCR method. This method involves reverse transcription of the mRNA, followed by second strand synthesis and PCR amplification of the resulting double-stranded DNA. See, for example, Shuldiner et al. "RNA Template-Specific Polymerase Chain Reaction" in METHODS IN MOLECULAR BIOLOGY, VOL. 15: PCR PROTOCOLS: CURRENT METHODS AND APPLICATIONS, B. A. White (ed), pages 169–176, and references therein.

Analysis of patterns of expression of the protein product of the gene of interest in plant tissue may be achieved by means of immunohistochemistry, using a monoclonal or polyclonal antibody preparation specific for the protein of interest. Levels of expression of the protein corresponding to the gene of interest may be measured by means of Western blots, using protein prepared from the whole plant or from particular organelles of the plant. Those of skill in the art can readily devise other methods of analyzing the phenotype of the $F_2$ plants described above. It should also be noted that the present invention permits all members of a gene family to be disrupted. Although any single disrupted gene may not produce a mutant phenotype, combinations of double mutants can be easily made, using conventional breeding techniques, and detected by PCR as described above.

The present invention, thus generally described, will be understood more readily by reference to the following examples, which are provided by way of illustration and are not intended to be limiting of the present invention.

EXAMPLE 1
PREPARATION OF GENOMIC DNA FROM $F_1$ PLANTS

Zea mays leaf punches were collected using a handheld leaf punch and lyophilized. Six punches of leaf tissue were collected per plant, in 1.2 ml polypropylene tubes, and placed in appropriate positions in 96-well plates. Two stainless steel, oil-free ballbearings (5/32 of an inch) were added to each tube. The tubes were centrifuged briefly to position the ballbearings at the bottom of the tube.

Using a flat surface, all of the tubes in the 96-well plate were firmly pressed down so that the tops of the tubes were level. The tubes were then sealed with mylar using a heat sealer at approximately 380° C. The plates were then shaken for 30 seconds using a modified jigsaw adapted for rapid, high torque shaking of the sample tubes. The plates were shaken for 30 seconds to macerate the plant tissue, and then 600 l of extraction buffer was added to each tube. The extraction buffer consisted of 0.2M trisodium citrate, 0.01M DTPA (diethylenetriaminepentaacetic acid) (free acid), 0.8M LiCl, 0.5% PEG (polyethylene glycol 8000), and 0.005M o-phenanthroline monohydrate. DNA extraction buffer was sterile filtered before use, and stored in dark plastic without a stir bar at 4° C. The tubes were resealed, shaken again as above, and then heated for 45 seconds per plate in a conventional microwave oven at high power. The plates were then centrifuged for 15 minutes at 4000 rpm. A storage plate was then prepared containing 120 $\mu$l isopropanol. 200 $\mu$l of the supernatant from the spun sample tubes was then added to 120 $\mu$l of the isopropanol. The tubes containing the isopropanol/supernatant mixture were mixed and spun in a centrifuge at 4000 rpm for 15 minutes. Following centrifugation, the isopropanol was decanted, and the plates tipped upside-down and tapped on blotting paper in order to remove as much isopropanol as possible. The pellets were dried for approximately two hours. When the pellets were dry, 50 microliters of storage buffer were added to each well. The storage buffer consisted of 10 mM Tris base, 10 mM EDTA (disodium), 0.01% Triton-X 100, with a final pH of 8.0 adjusted with NaOH. The Triton-X 100 may be left out if the DNAs will not be transferred using a pinning apparatus. Following addition of storage buffer, the microtiter plates were heated at 65° C. for 10 minutes to resuspend the pallets. Following heating, the microtiter plates were sealed with mylar using a heat sealer at approximately 380° C.

EXAMPLE 2
AMPLIFICATION BY PCR OF $F^1$ DNA

Polymerase chain reaction was performed in 9X microtiter plates. The plates were stored at 65° C. to remove dissolved gases from the plates. Once plates have cooled to room temperature sufficient gas can reabsorb within a day to cause bubble formation in the PCR reaction. Alternatively, the plates may be degassed, filled, and then stored in an air tight manner so as to avoid reabsorption. In addition, a PCR buffer was used containing 0.01% Triton-X 100, and water which was degassed by boiling and storage under vacuum. In addition, immediately prior to placement of microtiter plates in the oven for PCR the microtiter plates were spun at approximately 2000 rpms for 30 seconds to remove bubbles. Alternatively, it is possible to visually monitor the plates for bubble formation at the bottom of the wells at approximately 60 minutes into the PCR reaction run. If bubbles are present, they can be removed by a brief spin in the centrifuge. The reaction cycle is interrupted as it begins the cooling phase, the plates are spun, and immediately returned to the oven.

The PCR "Hot Tub" buffer used in these PCR reactions was designed specifically to overcome the challenges of high heat, changes of magnesium (Mg) ion concentration, and low amounts of DNA template. Use of the buffer described in these experiments has significant advantages over the buffer supplied with the commercial "Hot Tub" enzyme when PCR reactions are run in Biotherm™ ovens, with less DNA than optimal, or with some carryover chelator from the template DNA preparation.

Citrate has a $K_m$ for Mg ions at about the desired concentration required for the Hot Tub enzyme. It thus acts as an excellent Mg concentration buffer. About half of the 20 mM Mg in the buffer is chelated by the citrate, leaving the final Mg concentration stabilized at about 10 mM. Sucrose was determined to be the most effective reagent to stabilize the polymerase enzyme at high heat. When carrying out a PCR in Biotherm ovens, some of the outer wells may overheat when bringing the interior wells to the required temperature. Addition of sucrose to the buffer protects the polymerase enzyme in these outer wells. Furthermore, $MgSO_4$ is used instead of $MgCl$, as the presence of chloride ion has shown deleterious effects on the outcome of the PCR. Tris base and glycine are used to buffer the pH of the PCR solution at pH 9.2.

Histidine and other secondary and higher amines act as oxygen radical quenchers, and were shown to reduce the requirement for template DNA concentrations to well below 1 ng/$\mu$l of PCR reaction mixture. Finally, Triton-X 100 appears to have some enzyme heat stabilizing affect, and as noted above contributes greatly to elimination of bubbles. In its final form the Hot Tub PCR buffer consists of the following:

| | |
|---|---|
| Tripotassium Citrate | 20 mm |
| $MgSO_4$ | 20 mM |
| Tris base | 40 mM |
| Glycine | 10 mM |
| L-Histidine | 5 mM |
| Triton X-100 | 0.01% |

The pH of the buffer is adjusted to 9.2 with NaOH or KOH. Heating of the buffer is required to dissolve the histidine and sucrose. The buffer should not be filtered and should be stored at −20° C.

Four microliters of PCR reaction solution were added to each well. For large scale preparations a liquid handler, for example an IVEK™ machine can be used. The IVEK™ pumps were set at a setting of 7 in order to deliver approximately 4 μl/stroke. Only DC-200 silicone oil (Fluka) should be used. The oil may be made blue using approximately 200mg of Solvent Blue 35 (Aldrich). When using IVEK™ pumps, bubbles in the tubing are to be avoided. The IVEK™ was debubbled using distilled water, then loaded with 1x PCR buffer. The PCR mix was then prepared and placed in the tubing. The tube was then placed on the input port of the IVEK™ without introducing bubbles into the tube. The PCR mix used in the IVEK™ machine for a PCR reaction was as follows:

| | |
|---|---|
| primer 1 | 1 μM |
| primer 2 | 1 μM |
| dNTP | 240 μM |
| 10X Hot Tub buffer | 1X |
| Schilling Yellow | 1% |
| Hot Tub enzyme | 0.15 U/4 μl |
| Degassed sucrose | 10% |

The enzyme should be added last to a premixed solution. The dNTPs were found to be unstable, and were kept in single use containers at −80° C. and thawed only once. Primers are made to 100 μM as they are received, and stored at −20° C.

One nanogram of genomic DNA template per microliter of the PCR reaction solution was added to each well, using either a pinner tool or manual addition methods. In the present experiments, a specifically designed pinner tool was used to move small amounts of many samples with a high degree of reliability. Standard pinners have minimal surface area and will not hold small drops of liquid reliably. The pins used in these experiments were stainless steel BRASSELER™ dental burrs (friction grip H1-010 US #2) with carbide tips. Each tip has 6 concave slots which hold about 8 nl of liquid for a total of about 50 nl per pin. The pin will displace approximately 8 μl of the 20 μl volume capacity of a 9x plate well. Consequently, the amount of DNA solution in the well can be up to 12 μl. Wells containing 12 μl of DNA solution can thus be accessed over 200 times. A recommended DNA concentration for the solution is 100 ng/μl. Taken together with the large amount of DNA available from the leaf punches, as described in Example 1, this means that each pooled DNA solution in the 9X plate may be sampled for PCR at least 10,000 times. The slots at the tip of the burr are too small to accept liquids with high surface tension, such as water, and hence a surfactant must be used to reduce the surface tension or the pinner will function unreliably. Triton-X 100 at 0.01% was determined to be optimal, and therefore was included in the DNA storage buffer. The pins were designed so that all of the liquid is stored at the tip. Because of this, the volume held by the tip does not decrease as the volume of the DNA solution decreases, and the pins are extremely effective at moving the last quantities of the DNA solution from the well. Alternative pins for use in the method of the invention are the 6801-010 diamond burr pins. The many internal angles between the diamond and the embedding epoxy of such pins gives this tip more reliability than the six internal slots of the carbide burr.

In order to carry out the pinning, the pinner was fastened securely to a jig. The DNA source plate and the reception plate containing the PCR mix were placed in the jig in the same orientation, so that appropriate wells were pinned with the matching pin. The pinner was pressed into the DNA plate two or three times in order to wet the pins. The pinner was then moved to the reception plate and pressed into the plate three or four times fairly vigorously in order to move the DNA solution through the oil overlay. The pinner must not be returned to the DNA source plate after it is contaminated with oil and PCR mix, and must be thoroughly cleaned before reuse. The PCR plate was then spun at 2000 rpm for a few seconds in order to place the PCR mix and oil at the bottom of each well. The PCR was carried out in a Biotherm™ oven. The following suggested profile presents temperatures as measured by the oven's temperature probe in the air inside the oven:

| Time | Temp | Ramp Speed |
|---|---|---|
| 2 min | 99 | 2° C./sec |
| 1 min | 96 | 2° C./sec |
| 3 min | 55 | 2° C./sec |
| 6 min | 72 | 2° C./sec |

The initial 99° setting was to move the plate toward a denaturation temperature. As the edges of the plate approach 96° C. the temperature was dropped to 96° C. for one minutes in order to allow the center of the plate to catch up with the edges. The same concept was applied in cooling the plate. As the edges of the plate approach approximately 55° C., the air temperature was brought to 55° C. to equilibrate the center of the plate, and the temperature was then moved slowly through the likely oligonucleotide hybridization temperatures. Unusually long times at the extension temperature may sometimes be advantageous. The Hot Tub enzyme has a temperature optimum at 70° C., and this temperature was obtained with an approximate oven air temperature of 72° C.

EXAMPLE 3
DETECTION OF AMPLIFIED DNA PRODUCTS

Due to the fact that the signal and signal/noise ratio limiting aspect of the method of the present invention is the amount of PCR DNA on the membranes, and further due to the fact that this amount of DNA is also limiting for hybridization time, spin or centrifugation "dot blotting" was developed as an alternative to pinning dot blots. This alternative was found to be superior because it can transfer all of the PCR solution to the filter much faster than the repeated applications which are required by using a pinner. This method also overcomes the problems of discarding the oil overlay.

Following PCR the microtiter plates were removed from the Biotherm™ ovens. A series of membrane and blotting pad layers were then overlaid on the top of the PCR microtiter plates. This was accomplished in the following manner: first, the membranes were labeled for identification and orientation using a VWR biotech marker on a uniform selected side. Zeta-Probe (Bio-Rad) membranes were rinsed and soaked in distilled water. The PCR microtiter plate was wiped with a tissue in order to remove excess surface oil. Two membranes were then blotted to remove standing water and placed on the top of the PCR plate in the appropriate orientation, and covered with a plastic sheet. The plastic surface is then rubbed to remove excess water and any entrapped air bubbles between the filters or between the filters and the plate. A wetted blotting pad was blotted to remove standing water, placed on top of the plastic covered membrane layers, and then itself covered with plastic and rubbed in order to force contact with the membranes. A second blotting pad, this one dry, was placed an top of the water soaked blotting pad, and the entire plate-membrane-blotting pad structure was inverted and centrifuged at approximately 1800 rpm for two minutes, or until little or no liquid phase remains in the plate. The sandwich was then removed from the centrifuge, and the two blotting pads were removed and discarded. It was found to be critical at this stage not to disturb the membranes on the plate. The oil which had been forced against the membrane was replaced into the plate by re-inverting the sandwich and centrifuging the oil to the bottom of the wells at 1800 rpm for a few seconds.

The membranes then were removed and pre-treated for hybridization. The membranes were placed DNA-face up carefully on the surface of a blotting pad soaked with 0.6M NaCl, 0.4M NaOH for about two minutes. Filters were then moved again, DNA face up, to a pad soaked with 0.5M Tris at pH 7.5, and 1.5 m NaCl. Air bubbles between the membrane and the blotting pad were detected by watching the color of the red dye on the membrane. This dye is a pH indicator. The membranes were then fixed to the membranes using a Stratalinker (Stratagene) at 200µJ, and baked in a vacuum oven at 80° C. for 2 hours.

Although Zeta-Probe filters were found to work particularly well in the method of the invention, other positively charged nylon filters would also be suitable. The blotting pads must be soft and smooth enough to conform tightly to the surface of the membrane, and porous enough to allow liquid to easily pass through.

Preparation of radiolabeled probe by the standard random hexamer priming protocol method and hybridization to the membranes were both carried out by standard methods known in the art. See, for example, CURRENT PROTOCOLS IN MOLECULAR BIOLOGY, Ausubel et al. (eds), pages 2.10.2–3 and 3.5.9–10.

What is claimed is:

1. A method for associating a mutant phenotype of an F2 progeny plant with the presence of an insertion sequence inserted within or close to a gene of known sequence of said F2 progeny plant, comprising the steps of:

(a) crossing two parent plants, one of which contains an insertion sequence, to produce a plurality of F1 progeny plants at least some of which are heterozygous for insertion of said insertion sequence within or close to said gene;

(b) analyzing by PCR amplification, genomic DNA of said plurality of F1 progeny plants to detect the presence of said insertion, wherein genomic DNA of each F1 progeny plant of said plurality is referenced to an individual F1 progeny plant and wherein said genomic DNA is PCR amplified using two oligonucleotide primers with one of said primers annealing to said gene and the other primer annealing to said insertion sequence, and whereby said PCR amplification is obtained only when said insertion occurs within or close to said gene;

(c) producing a plurality of F2 progeny plants by self-fertilizing said plurality of F1 progeny plants, wherein genomic DNA from each of said F1 progeny plants is directly referenced to its F2 progeny plants; and, (d) associating said mutant phenotype of said F2 progeny plant that differs from the phenotype of said F1 progeny plants with the homozygous presence of said insertion sequence inserted within or close to said gene of said F2 progeny plant.

2. The method of claim 1, wherein said insertion sequence comprises a terminal invested repeat sequence.

3. The method of claim 1, wherein said insertion sequence is a member of the Mutator family.

4. The method of claim 1, wherein said plants are corn plants.

5. The method of claim 1, wherein the size of said plurality of said F1 progeny plants statistically favors an insertion of said insertion sequence into substantially any gene of said F1 progeny plants.

6. A composition for associating a mutant phenotype of an F2 progeny plant to the presence of an insertion sequence inserted within or close to a gene of known sequence of said F2 progeny plant, comprising:

(a) a collection of genomic DNA prepared from a plurality of F1 progeny plants produced by the crossing of two parent plants one of which contains an insertion sequence, wherein said plurality of F1 progeny plants collectively contain a plurality of said insertion sequences inserted within or close to a plurality of different genes such that at least some of said F1 progeny plants are heterozygous for insertion of said insertion sequence into said gene of known sequence and wherein genomic DNA of each F1 progeny plant of said plurality is individually identifiable in said collection of genomic DNA;

(b) a collection of F2 progeny seed obtained by self-fertilization of said plurality of F1 progeny plants, wherein said F2 progeny seed from each of said F1 progeny plants are individually identifiable in said collection, and wherein each F1 progeny plant genomic DNA of (a) is referenced to individually identifiable F2 progeny seed of (b).

7. The composition of claim 5, further comprising at least one primer pair, wherein one of said primers anneals to said gene and the other primer anneals to said insertion sequence.

8. The composition of claim 6, wherein the size of said plurality of F1 progeny plants statistically favors an insertion of said insertion sequence into substantially any gene of said F1 progeny plants.

9. The composition of claim 6, wherein said insertion sequence comprises a terminal inverted repeat sequence.

10. The composition of claim 6, wherein said insertion sequence is a member of the Mutator family.

11. The composition of claim 6, wherein said plants are corn plants.

* * * * *